US009005120B2

(12) United States Patent
Ryan

(10) Patent No.: US 9,005,120 B2
(45) Date of Patent: Apr. 14, 2015

(54) VITAL SIGNS MONITORING USING PERSONAL PROTECTIVE EQUIPMENT

(76) Inventor: Richard H. Ryan, Sherman Oaks, CA (US)

(*) Notice: Subject to any disclaimer, the term of this patent is extended or adjusted under 35 U.S.C. 154(b) by 916 days.

(21) Appl. No.: 12/396,233

(22) Filed: Mar. 2, 2009

(65) Prior Publication Data

US 2009/0221884 A1 Sep. 3, 2009

Related U.S. Application Data

(60) Provisional application No. 61/032,895, filed on Feb. 29, 2008.

(51) Int. Cl.
*A61B 5/00* (2006.01)
*A61B 5/02* (2006.01)
*A61B 5/01* (2006.01)
(Continued)

(52) U.S. Cl.
CPC . *A61B 5/682* (2013.01); *A61B 5/02* (2013.01); *A61B 5/0008* (2013.01); *G06F 19/3418* (2013.01); *A63B 2230/04* (2013.01); *A63B 2230/08* (2013.01); *A63B 2230/20* (2013.01); *A63B 2230/50* (2013.01); *A63B 2071/088* (2013.01); *A61B 5/0002* (2013.01);
(Continued)

(58) Field of Classification Search
CPC ...... A61B 5/0002; A61B 5/0008; A61B 5/02; A61B 5/1455; A61B 5/682; G06F 19/3418; A63B 71/085; A63B 2230/04; A63B 2230/08; A63B 2230/20; A63B 2230/50; A63B 2071/088
USPC ........ 2/1, 455, 2.5, 410, 5, 6.1, 6.6, 425, 205; 600/300–301, 307, 308, 309, 344, 349, 600/372, 386, 474, 552–555, 587, 589–590
See application file for complete search history.

(56) References Cited

U.S. PATENT DOCUMENTS 4,044,762 A 8/1977 Jacobs
4,510,941 A * 4/1985 Semrow et al. ............... 600/484
(Continued)

OTHER PUBLICATIONS

NPL_RyanHall_2007, p. 1-4.*
(Continued)

*Primary Examiner* — William Thomson
*Assistant Examiner* — Marie Archer
(74) *Attorney, Agent, or Firm* — Thomas A. Runk; Fulwider Patton LLP

(57) ABSTRACT

A vital signs monitor system is integrated with personal protective equipment ("PPE") so that upon wearing the PPE, the monitor is placed in an operational position to monitor a vital sign. In one embodiment, the vital signs sensor comprises a thermal sensor located at a mouth guard to automatically make operational contact with tissue under the tongue when the mouth guard is worn. A second vital signs monitor comprising reflective pulse oximetry devices senses oxygen saturation and heart rate. Vital signs data are communicated to an RF module located in an associated helmet for transmission to a remote location. A gateway at that remote location receives the transmitted vital signs data and forwards that data to a data collection, organization, and access system that is programmed to make the vital signs data available over the Internet. Medical personnel, coaches, supervisors at the location of the PPE can monitor the vital signs of the wearer by accessing the data collection, organization, and access system with hand held, or portable computing equipment over the Internet.

16 Claims, 8 Drawing Sheets

(51) Int. Cl.
  *G06F 19/00* (2011.01)
  *A63B 71/00* (2006.01)
  *A63B 71/08* (2006.01)
  *A61B 5/145* (2006.01)

(52) U.S. Cl.
  CPC  *A61B 5/01* (2013.01); *A61B 5/145* (2013.01); *A63B 71/085* (2013.01); *Y10S 128/903* (2013.01)

(56) References Cited

U.S. PATENT DOCUMENTS

| | | | |
|---|---|---|---|
| 4,947,490 A | | 8/1990 | Hayden |
| 5,062,432 A | | 11/1991 | James et al. |
| 5,353,810 A | | 10/1994 | Kittelsen et al. |
| 5,546,609 A | | 8/1996 | Rush, III |
| 5,642,735 A | | 7/1997 | Kolbly |
| 5,692,523 A | | 12/1997 | Croll |
| 5,706,428 A | * | 1/1998 | Boer et al. ............... 370/342 |
| 5,931,164 A | | 8/1999 | Kiely et al. |
| 6,584,978 B1 | * | 7/2003 | Brett et al. ............... 128/859 |
| 6,785,568 B2 | | 8/2004 | Chance |
| 6,826,509 B2 | | 11/2004 | Crisco, III et al. |
| 6,934,971 B2 | | 8/2005 | Ide et al. |
| 6,941,952 B1 | | 9/2005 | Rush, III |
| 7,188,151 B2 | | 3/2007 | Kumar et al. |
| 7,299,804 B2 | | 11/2007 | Kittelsen et al. |
| 7,311,666 B2 | * | 12/2007 | Stupp et al. ............... 600/300 |
| 7,481,773 B1 | * | 1/2009 | Dorroh et al. ............ 600/549 |
| 2002/0148470 A1 | | 10/2002 | Blue et al. |
| 2003/0040679 A1 | | 2/2003 | Weber et al. |
| 2003/0154990 A1 | | 8/2003 | Parker |
| 2004/0076219 A1 | * | 4/2004 | Madison et al. ........... 374/159 |
| 2004/0181166 A1 | * | 9/2004 | Williford et al. .......... 600/549 |
| 2005/0059869 A1 | | 3/2005 | Scharf et al. |
| 2005/0113654 A1 | * | 5/2005 | Weber et al. .............. 600/309 |
| 2005/0113656 A1 | | 5/2005 | Chance |
| 2005/0177335 A1 | | 8/2005 | Crisco, III et al. |
| 2005/0177929 A1 | | 8/2005 | Greenwald et al. |
| 2006/0074338 A1 | | 4/2006 | Greenwald et al. |
| 2006/0125623 A1 | | 6/2006 | Appelt et al. |
| 2006/0189852 A1 | | 8/2006 | Greenwald et al. |
| 2006/0202816 A1 | * | 9/2006 | Crump et al. ........... 340/539.12 |
| 2006/0276864 A1 | * | 12/2006 | Collins .................... 607/105 |
| 2007/0028370 A1 | | 2/2007 | Seng |
| 2007/0106172 A1 | | 5/2007 | Abreu |
| 2007/0191691 A1 | | 8/2007 | Polanco |
| 2008/0023002 A1 | | 1/2008 | Guelzow et al. |
| 2008/0058621 A1 | | 3/2008 | Melker et al. |
| 2009/0149722 A1 | * | 6/2009 | Abolfathi et al. ......... 600/301 |
| 2009/0210032 A1 | * | 8/2009 | Beiski et al. ............. 607/59 |
| 2009/0227852 A1 | * | 9/2009 | Glaser .................... 600/324 |

OTHER PUBLICATIONS

Tattersall et al, "Hypoxia reduces the hypothalamic thermogenic threshold and thermosensitivity" J Physiol 587.21 (2009) pp. 5259-5274.*

Tripp, Jr. et al., United States Statutory Invention Registration No. H1039, Published Apr. 7, 1992.

* cited by examiner

FIG. 3
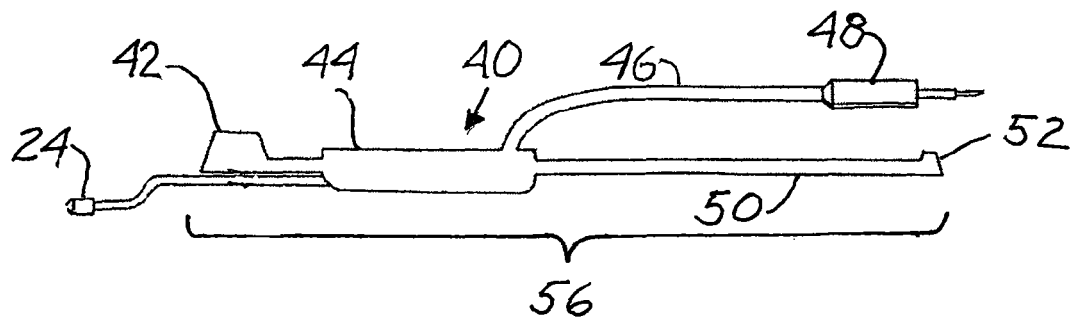
FIG. 4
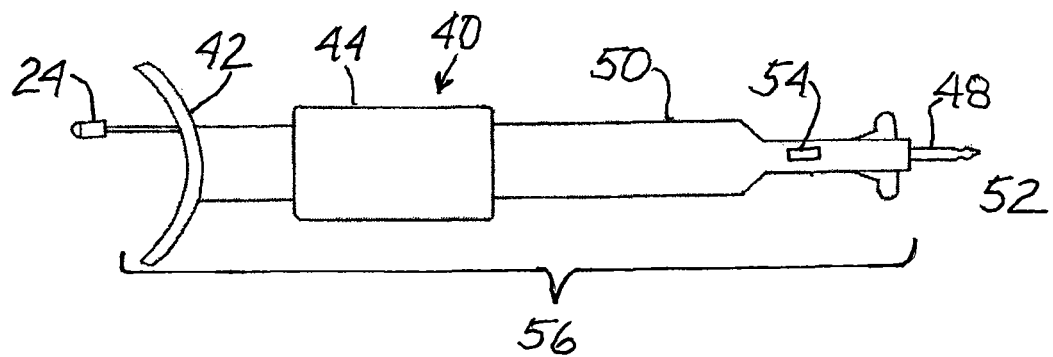
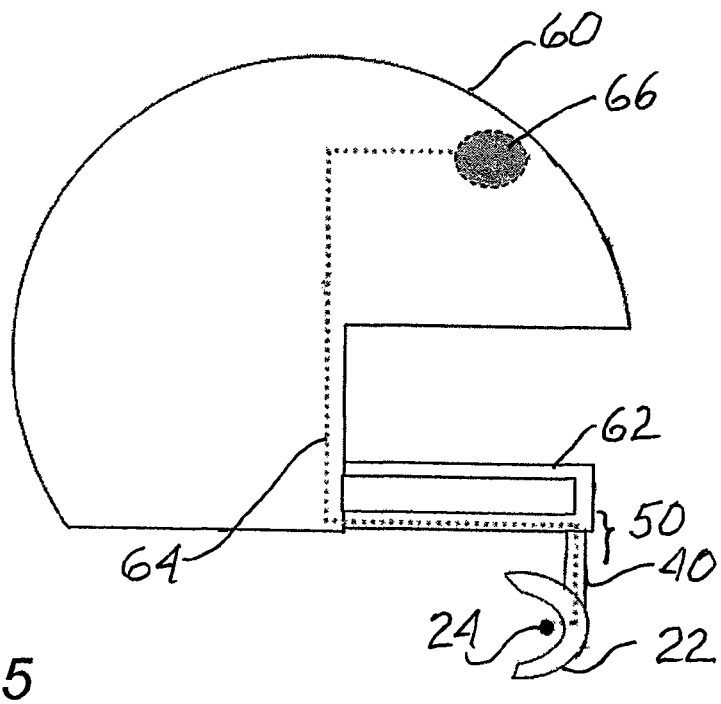
FIG. 5

VITAL SIGNS MONITORING USING PERSONAL PROTECTIVE EQUIPMENT

CROSS-REFERENCES TO RELATED APPLICATIONS

This application claims the benefit under 35 U.S.C. §119(e) of U.S. Provisional Application No. 61/032,895 filed Feb. 29, 2008, which is incorporated herein by reference in its entirety.

The present invention relates generally to monitoring vital signs of a person, and more particularly, to incorporating vital signs sensing into personal protective equipment.

BACKGROUND

Participation in athletic activities can expose the participants to physical harm. Collisions between participants frequently occur in certain sports (e.g., football, field hockey, lacrosse, ice hockey, and the like) which can cause physical harm and as a result, personal protective equipment ("PPE") has been developed. Mouth guards are coverings worn over the teeth to protect against concussion during participation in sports, and in doing so, the teeth also receive protection. The use of mouth guards is well known. Additionally, the use of helmets in a variety of different sporting events is well known, and in many cases is mandatory. The primary purpose of these helmets is to protect a wearer's head from injury in the event that it is exposed to force. Such helmets typically have a hard outer shell that covers an energy-absorbing material. The outer shell typically covers an expanded inner layer that lies between the outer shell and the wearer's head. The inner layer is intended to absorb energy in the event it becomes necessary in order to minimize the energy transmitted to a wearer's head. Consequently, there is space between the wearer's head and the outer shell.

Injury to athletes can also occur when competition for prolonged periods in an abnormally high temperature environment is conducted. Football, lacrosse, and other sports may require high levels of exertion from the athletes for substantial time periods in elevated temperatures. Such exertion levels coupled with high temperatures also have the potential to injure a person.

Individuals such as steel mill and power plant workers and heavy machine operators perform duties in such environments and can be exposed to considerable risk of illness and/or injury due to heat stress. These particular environments can involve elevated temperatures, but exposure to undue low temperatures can also result in problems, for example hypothermia. Workers who perform duties in the environments mentioned above may also have specialized PPE, some of which may include an enclosed protective suit. Such suits may contribute to an increased heat level to the worker thereby increasing the amount of heat stress. In addition, because the workers are enclosed in such suits, external temperature monitoring devices would not be reliable either from an actual body temperature sensing standpoint or from the standpoint of providing a readily available signal of elevated temperatures to the worker.

Past efforts to protect against such heat stress have included monitoring the environmental condition per se that is the ambient temperature, radiant heat, humidity, etc. However, such monitoring only indirectly indicates the possible temperature of the person.

It has been recognized that internal body temperature is an accurate parameter for assessing heat stress. Continuous monitoring of the internal temperature by means of a well-placed thermometer could provide useful and direct information about a person. There have been efforts to use skin temperature and heart rate as parameters in assessing internal temperature. These prior approaches have various shortcomings in that they are uncomfortable, difficult to use, and in some cases, lack reliability, and accuracy. Sensing oxygen saturation of the blood also assists in determining the well-being of a person. Oxygen is the most essential element to life; no human life thrives in the absence of oxygen. Sensing a person's temperature and oxygen saturation unobtrusively would be helpful in determining a person's vital signs and useful in determining the well being of that person.

In sports and other activities having mandatory PPE, such as mouth guards and helmets, it would be desirable to also install an instrument or instruments that can monitor a person's vital signs for heat stress. Such monitoring could lead to increased safety. Because the athlete or worker must wear the PPE in any case, an unobtrusive incorporation of the sensor or sensors and other vital signs equipment would assist in monitoring the person's well being under the actual conditions the person is experiencing. Additionally, because such athletes or workers must be unrestrained in their movements, wirelessly transmitting the vital signs information from the PPE sensors to a remote location for monitoring would be desirable.

Hence, those of skill in the relevant art have identified a need for monitoring a person's vital signs during competition or other activities so that unacceptable levels of heat stress or other stress can be detected before an adverse reaction occurs. Those skilled in the art have also recognized a need for accurate, reliable, easy-to-use, and physically unobtrusive monitoring of vital signs. Further needs for remote monitoring of vital signs and wireless communications of relevant data have also been recognized. The invention fulfills these needs and others.

SUMMARY OF THE INVENTION

Briefly and in general terms, the present invention is directed to incorporating a vital signs sensor in personal protective equipment ("PPE") for sensing a selected target physiological site of a person, conducting vital signs sensor signals developed from sensing the target physiological site to a transmitter located in the PPE, and transmitting the sensor signals to a remote receiving site. In yet further detailed aspects, a temperature sensor is located in a first PPE device worn while the person is participating in an activity, the PPE device having a vital signs sensor disposed in the PPE in a way that it is located at the target physiological site of the person, the signals from which indicate a physiological characteristic or the vital sign of the person, said signals being transmitted to the remote location. In more detailed aspects, the temperature sensor is located internally to the person, and is in continuous contact with tissue of the person. In another aspect, the vital signs sensor continuously provides sensor signals indicative of the vital signs sensed.

In additional detail, a second sensor is located in a second PPE device continuously worn while the person is performing the activity, the second sensor disposed such that the person's vital sign from a second target physiological location is sensed, and such sensor signals also being transmitted to the remote location.

In another aspect, a plurality of vital signs sensors are used, all of which develop sensor signals representative of physiological characteristics of a person, and all of which are communicated to a transmitter for transmission to a remote site. In another detailed aspect, an SPO$_2$ sensor is used for sensing the oxygen saturation in the blood of a person. In yet another more detailed aspect, a reflective SPO$_2$ sensor (RPO sensor) is used to sense the person's vital sign. In accordance with even further details, the first sensor is disposed in a mouth guard and the second sensor is disposed in a helmet. The sensing mouth guard or mouthpiece includes a connector strap extending from the mouth guard to tether it to the helmet. The connector strap is adapted to secure the mouthpiece to the protective helmet and to provide protection to any wires that may connect the physiologic sensor in the mouth guard with processing and transmitting equipment in the helmet. The strap may be used to either permanently secure the mouthpiece to the helmet or removably secure the mouthpiece. In the case of a removable mouth guard, electrical connectors may be used between the wires in the mouth guard and the wires in the helmet. The second vital signs sensor is disposed in the helmet and directed to the head of the athlete to sense SPO$_2$. In further detail, the second sensor comprises a reflective SPO$_2$ sensor (RPO sensor).

In accordance with another aspect of the present invention, the vital signs data signals from the vital signs monitoring system and PPE are received at a location remote from the person being monitored (e.g., on a sideline of the competition field of the athletic event). Those received signals may be received by a gateway to a network, such as the Internet, and transmitted to a data collection, organization, and access system. Persons, such as coaches and medical personnel, at the sidelines of the competition field can connect to the data collection system and monitor the vital signs of each player wearing the vital signs monitoring PPE. With such an arrangement, it is possible to monitor multiple athletes or multiple workers from a single computer screen.

The features and advantages of the invention will be more readily understood from the following detailed description which should be read in conjunction with the accompanying drawings.

BRIEF DESCRIPTION OF THE DRAWINGS

FIG. 3 is a side view of the tether of FIGS. 1 and 2 without the mouth guard showing the thermal sensor probe, the mouth guard mounting device, a data controller, a mechanical strap for attachment to the face guard of a helmet for example, a wire for conducting temperature data, and a plug for electrical connection to a socket located in a helmet;

FIG. 4 is a top view of the tether of FIG. 3;

FIG. 5 is a side view of a helmet showing the tethered mouth guard with temperature sensor and in dashed lines, the electrical connection to a transceiver mounted in the helmet for wireless transmission of temperature sensor data to a remote receiver;

DETAILED DESCRIPTION OF THE PREFERRED EMBODIMENTS

Figure 1:
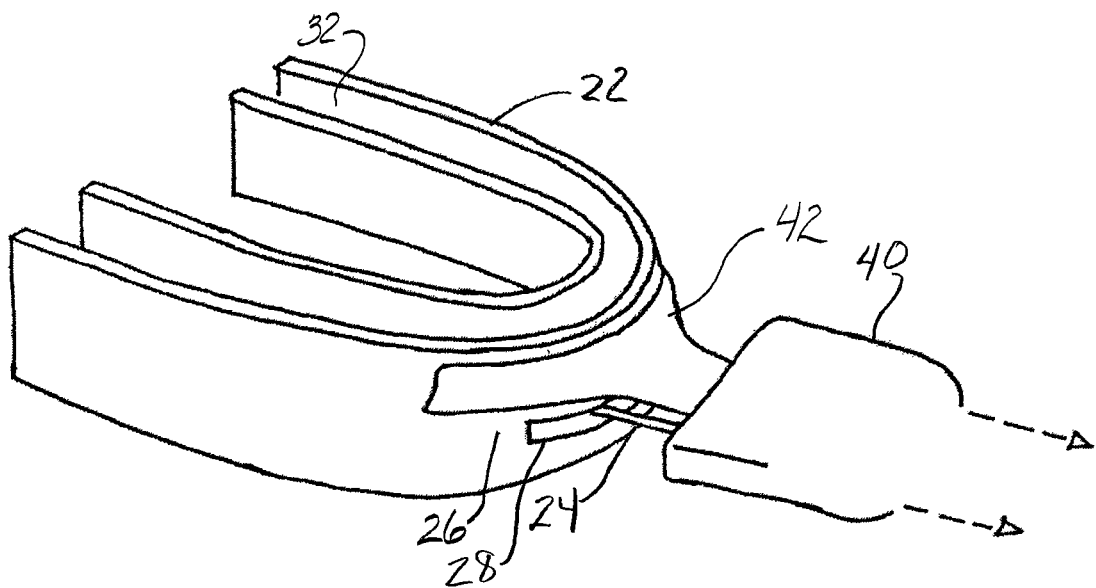
FIG. 1 is a perspective view of a mouth guard for protecting both the upper and lower rows of teeth showing the connection of a flexible tether and the thermal sensor probe mounted through an opening to rest under the user's tongue, also showing a partial view of the tether processor.
Figure 2:
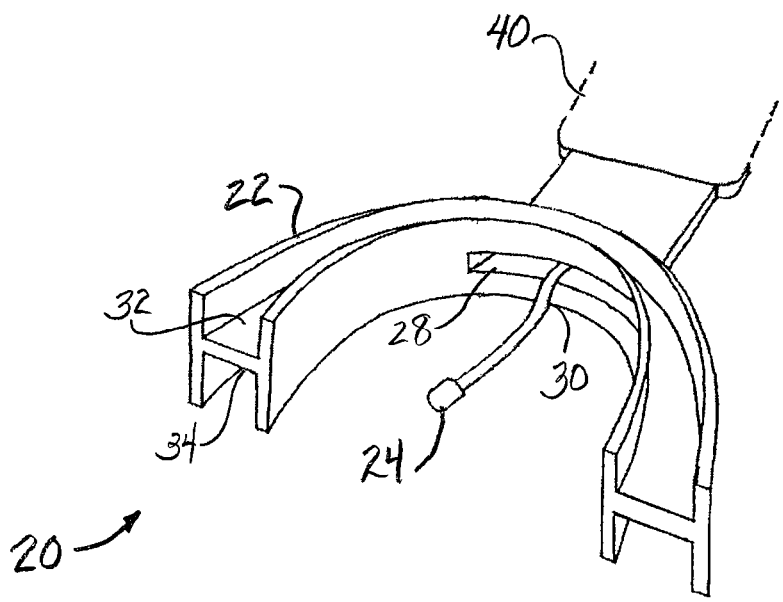
FIG. 2 is a rear view of the mouth guard of FIG. 1 showing the thermal sensor probe extended through an opening in the front of the mouth guard so that the probe may rest under the wearer's tongue to sense the wearer's internal oral temperature, also showing a partial view of the tether processor.

Referring now in more detail to the exemplary drawings for purposes of illustrating embodiments of the invention, wherein like reference numerals designate corresponding or like elements among the several views, there is shown in FIGS. 1 and 2 a vital signs monitoring system 20 mounted in personal protective equipment (PPE), in this case a mouth guard 22. In this embodiment, a thermal sensor 24 is positioned through an aperture 28 the front edge 26 of the mouth guard. The thermal sensor is curved 30 downward so that it will be positioned under the wearer's tongue when the mouth guard is in place. This will cause the thermal probe to come into contact with the internal oral tissue of the wearer to provide temperature data about the oral cavity of the person wearing the mouth guard. In this case the mouth guard 22 has been formed with an upper channel 32 and a lower channel 34 to accept both the wearer's upper row of teeth and lower row of teeth, respectively.

The mouth guard 22 is coupled to a controller module 40. In this case the controller module is mounted to the front edge 26 of the mouth guard and provides support for the thermal sensor 24 extending through the mouth guard into contact with the wearer's oral tissue. In one embodiment, the controller module comprises a mounting device 42 that is permanently bonded to the front edge 26 of the mouth guard 22, although other forms of attachment may be used. Although multiple sources exist for a thermal sensor with controller, for one embodiment such devices were obtained from Ningbo Jinlong Import & Export Co., Ltd, 2 Floor No. 40, Liuzhuang Alley, Ningbo, CHINA, Tel: 0086-574-87065201. The part no. was TSM-PCA-100. In another embodiment, the mounting device 42 may be releasably connected to the mouth guard so that the mouth guard may be replaced when needed while the controller module 40 is reusable.

Turning now to FIG. 3, a side view of the controller module 40 is shown. The thermal sensor 24 is mounted to the electronics case 44 and is internally wired to the electronics therein. In this case, the electronics comprise a temperature processor which will be discussed below. Power for the electronics and sensor are supplied through the cable 46 and plug 48 shown. A flexible strap 50 having a distal end 52 that can be bent back towards the case 44 is also mounted to the case. As shown in FIG. 4, which is a top view of the controller module of FIG. 3, the strap includes a locking aperture 54 along its length to receive the end 52 of the strap so that the strap may be placed around another object and form a tether 56 for the vital signs monitoring system 20, including the controller module 40, and mouth guard 22. For example, the strap may be bent around a wire of a face guard 62 (FIG. 5) forming part of a helmet and pushed through the locking aperture. The controller module is then tethered to the face mask.

Alternatively, the free end of the connector strap 50 may form a loop around a portion of the face guard 62 of the helmet 60 to secure the mouth guard assembly to the helmet. The snap fastener assembly may be releasable so that the mouth guard assembly can be separated from the helmet. It is also contemplated that the fastener assembly may be a grommet or other more permanent fastener. It is also contemplated that the fastener assembly may directly attach the mouth guard assembly to the side of the helmet. Although not shown, electrical connectors may be used for any wires coming from or going to the mouth guard.

Such an arrangement is shown schematically in FIG. 5 in which a football helmet 60 is shown. The mouth guard 22, thermal sensor 24, and controller module 40 are tethered to the face mask 62 by means of the strap 50, although not shown in detail. The dashed line in FIG. 5 is meant to indicate appropriate wiring 64 between the thermal sensor 24 and an RF module 66 mounted at a higher location in the helmet. Electrical power, in the form of a battery or batteries (not shown) in one embodiment, is located at the RF module 66 and supplies the necessary power through the wiring 64 to permit the thermal sensor and electronics of the controller module to function. The power is conducted to the controller module through the plug 48 and cable 46. Although not shown in detail, the helmet includes an electrical socket at or near the face mask into which the controller module plug 48 is inserted to complete the necessary electrical circuits. The RF module 66 places the temperature data from the thermal sensor into the required protocol and transmits it from the helmet, as is discussed below in further detail.

Figure 6:
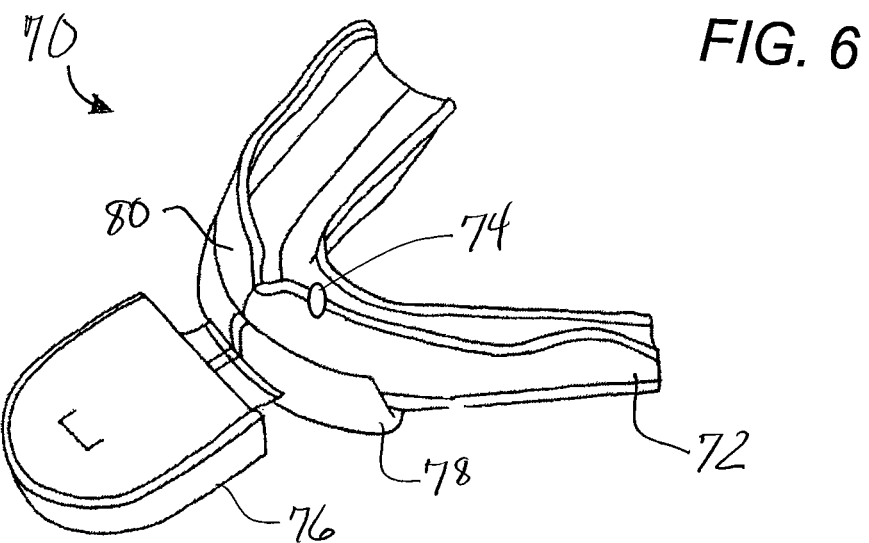
FIG. 6 is a perspective view of another embodiment of a mouth guard in which a temperature sensor is embedded for contact with oral tissues to provide internal oral temperature of the wearer. In this case, the mouth guard and sensor are connected and mounted to an electronics module containing a data controller and transceiver with an internal power supply for wirelessly transmitting temperature data signals.

FIG. 6 presents a second embodiment of a vital signs monitoring system 70 in which a second mouth guard 72 has a vital signs sensor 74 embedded in it. The vital signs sensor in this embodiment comprises a thermal sensor 74, as in FIG. 1. In this case, the thermal sensor is embedded so that the sensor portion is facing outward and is located at or near the top of the mouth guard. It will be noted that a custom mouth guard is shown for the top row of teeth of the wearer. This mouth guard is form fitted to the wearer such that it will remain in position on the upper teeth once installed. A thermal laminate type is shown, although other types of mouth guards may also be used. The mouth guard 72 has been formed such that when in position, the thermal sensor 74 will automatically be in contact with a mucosal membrane in the oral cavity of the wearer. This will provide an internal temperature (vital sign) of the wearer and the vital signs sensor has therefore become an integral part of the mouth guard personal protective equipment.

Figure 7:
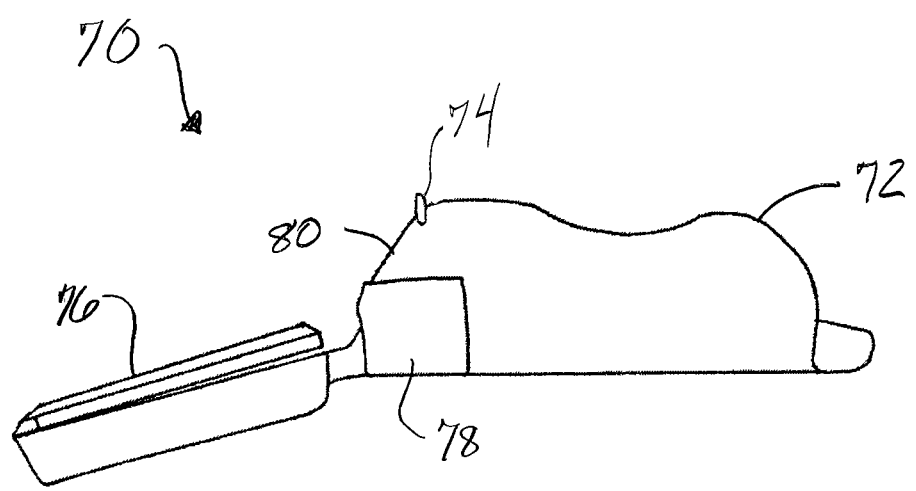
FIG. 7 is a side view of the mouth guard of FIG. 6 showing the placement of the temperature sensor so as to automatically make sufficient contact with a mucosal membrane of the mouth above the gum line when the mouth guard is correctly positioned on the wearer, also showing the attachment of the electronics module to the mouth guard.

As in FIG. 1, the mouth guard 72 of FIGS. 6 and 7 is connected to a controller module 76. A mounting device 78 mounts the controller module to the front edge 80 of the mouth guard. Although not shown, wiring from the thermal sensor 74 embedded in the mouth guard is routed through the mouth guard, through the mounting device 78, and into the controller module 76. In this embodiment, the controller module includes a microcontroller and an RF module (not shown), both of which are discussed in more detail below. The microcontroller receives the temperature signals from the thermal sensor and provides them to the RF module. The RF module then wirelessly transmits them to a transceiver 66 located in the helmet, as is shown in FIG. 5. Although FIG. 5 concerns a wired connection with the vital signs monitoring system 20 of that figure, the effective flow of signals and data for the wireless system 70 of FIGS. 6 and 7 would be similar; the difference being the wireless connection instead of the hard-wired connection.

FIG. 7 provides a side view of the vital signs monitoring system 70 of FIG. 6. The mouth guard 72 is shown with the thermal sensor 74 mounted at a relatively high position on the mouth guard. The controller module 76 is mounted to the front edge 80 of the mouth guard and at a downward angle, although in other embodiments, such configuration may differ.

Although the vital signs monitoring system 70 of FIGS. 6 and 7 is shown embedded in an upper mouth guard and having a wireless connection, this is for example purposes only. The mouth guard of FIGS. 6 and 7 may also be tethered in a manner similar to FIGS. 1 through 5 and may be wired to an RF module for remote transmission. Similarly, the sensor of FIGS. 1 and 2 may be used in a wireless configuration similar to the arrangement described for FIGS. 6 and 7.

It will be noted that in each of FIGS. 1 through 7, personal protective equipment PPE has been provided of which a vital signs system forms an integral part. In the cases of all of these figures, the PPE takes the form of a mouth guard and a helmet. Upon placing the respective mouth guard in its location in the wearer for which it was designed, the vital signs system is also automatically placed in an advantageous position in contact with internal tissue of the wearer. Thus the PPE has been fully integrated with the vital signs monitor so that both are functional when the PPE is correctly located in the wearer. It may be noted that the mouth guard of FIG. 2 differs from the mouth guard of FIG. 6. In the former case, the mouth guard is a dual row guard having a degree of flexibility to accept a wide range of sizes of teeth of wearers. It may also be a "boil and bite" type of mouth guard in which the mouth guard is boiled to a point where it softens sufficiently and is then "bit" by the wearer to customize it to the particular shape of the wearer's teeth. After the customization of the shape has occurred, the controller module 40 and thermal sensor 24 are mounted to it. In the case of FIG. 6, the mouth guard 72 takes the form of a thermal laminate. That is, the mouth guard is custom made for the wearer from the beginning. When the mouth guard construction is complete, the thermal sensor is embedded and the controller module mounted to it. Other types of mouth guards or other PPE may be used along with other ways to mount vital signs monitoring systems in the PPE.

Figure 8:
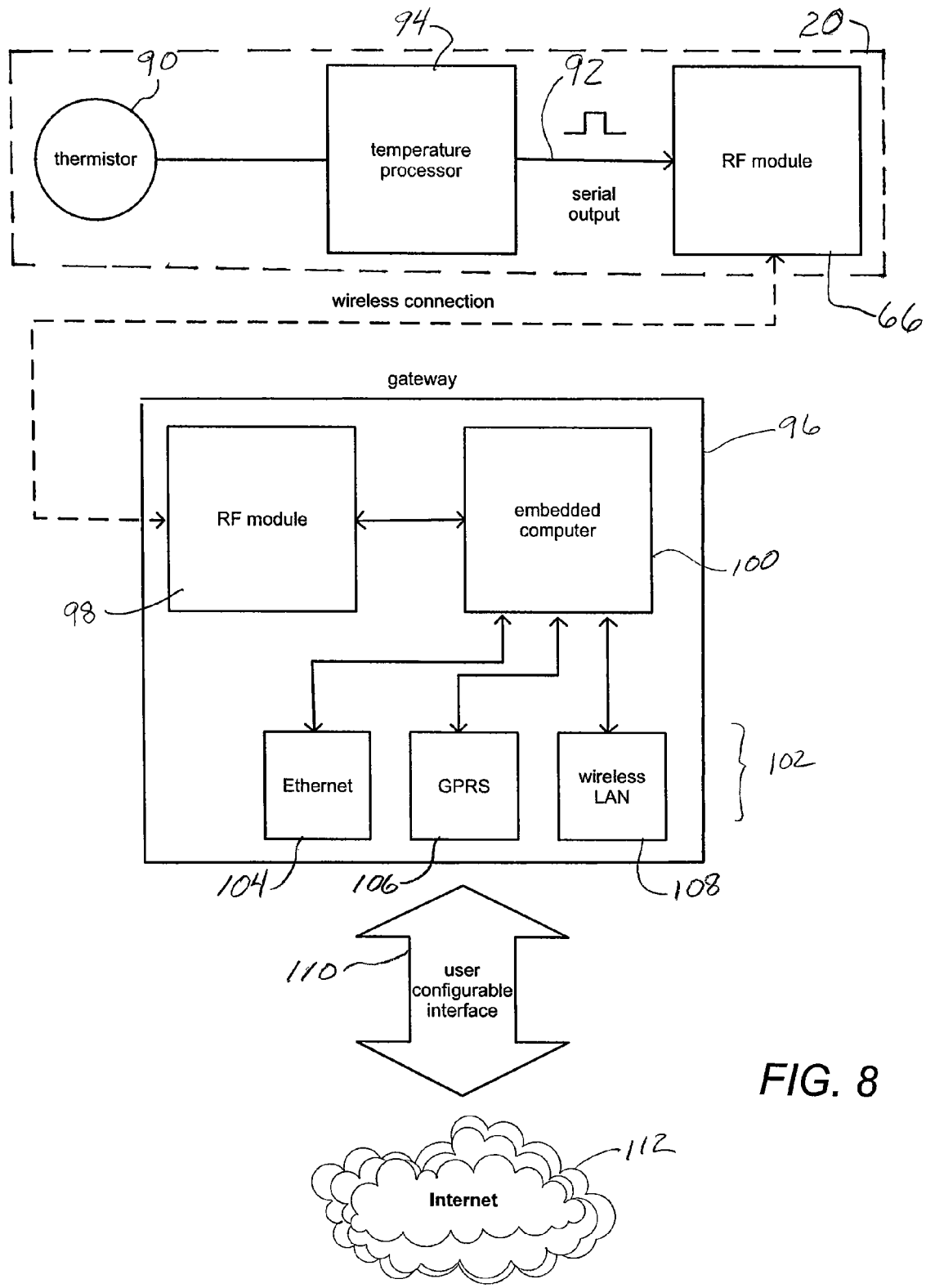
FIG. 8 is a block diagram of the flow of temperature data from the internal temperature sensor of the PPE shown in FIG. 1, comprising a mouth guard, through processing, receiving, and transmitting electronics to permit remote monitoring of the internal temperature of the person wearing the mouth guard.

FIG. 8 provides a block diagram of signal and data flow for the vital signs monitor system 40 of FIGS. 1 through 5 used with the PPE of a mouth guard 22, which is a wired system within the helmet 60. In this embodiment, the thermal sensor 24 comprises a thermistor 90, the signals of which are processed into a serial output 92 by a temperature processor 94. In one embodiment, the serial output 92 comprises temperature data signals. In some cases, the thermistor provides pre-processing of its signals yielding the serial output 92. In such cases, the temperature processor is an integral part of the thermistor unit. The serial output 92 is conducted in this case by wire to the RF module 66 shown in the helmet of FIG. 5. The RF module 66, depending on the application, may reformat the data signals and operate in accordance with the Zigbee specification or another. One of the main design constraints in the embodiments discussed and shown is low power use. Many of the modules and elements use coin-size batteries having a very limited amount of power. In the embodiments discussed and shown, low power circuits, standby status, low data rates, secure networking, and lowered expense are consistently employed to result in long battery life and secure networking. Zigbee is an attractive specification due to its low power usage and mesh networking which result in high reliability, longer range, and secure networking. However, other protocols or specifications are also usable. For example, where fewer monitors are used to receive the RF transmission from the helmet 60, the Bluetooth standard may be used.

After transmission by the RF module 66, the signals are received remotely by a gateway 96, defined here as a computer or a network that allows or controls access to another computer or network. In one embodiment, the gateway provides access to the Internet 112. A second RF module 98 receives the RF transmission from the helmet and provides the received signals containing temperature data to an embedded computer 100. That computer or other processing device then makes the temperature data available to one or more network or communication devices 102. In the case shown in FIG. 8, the embedded computer 100 makes the temperature data signals available to an Ethernet 104, a general packet radio service 106 (GPRS), and/or a wireless local area network 108 (LAN). More or fewer or different communication devices 102 may be provided depending on the application. A user configurable interface 110 is then used to control access by and to the gateway 96. The gateway communicates the temperature data to a network, such as the Internet 112, although other networks may be used.

Because gateways are commercially-available devices, no further details are provided herein. For example, suitable gateways can be obtained from Bluegiga Technologies, Inc. of 99 Derby Street, Suite 200, Hingham, Mass. 02043, U.S.A., having model nos. 3201, 2291, or 2293. The RF module 98 of the gateway 96 is selected to receive the transmitted signals from the PPE. For example, if the PPE transmits in Bluetooth or in Zigbee, the gateway must also have the capability to receive the signals. Although shown as the "Internet" 112 in FIG. 8, this is one example only. Other networks presently existing or developed in the future may be used. It is not the inventor's intention to limit the network to only the Internet.

Figure 9:
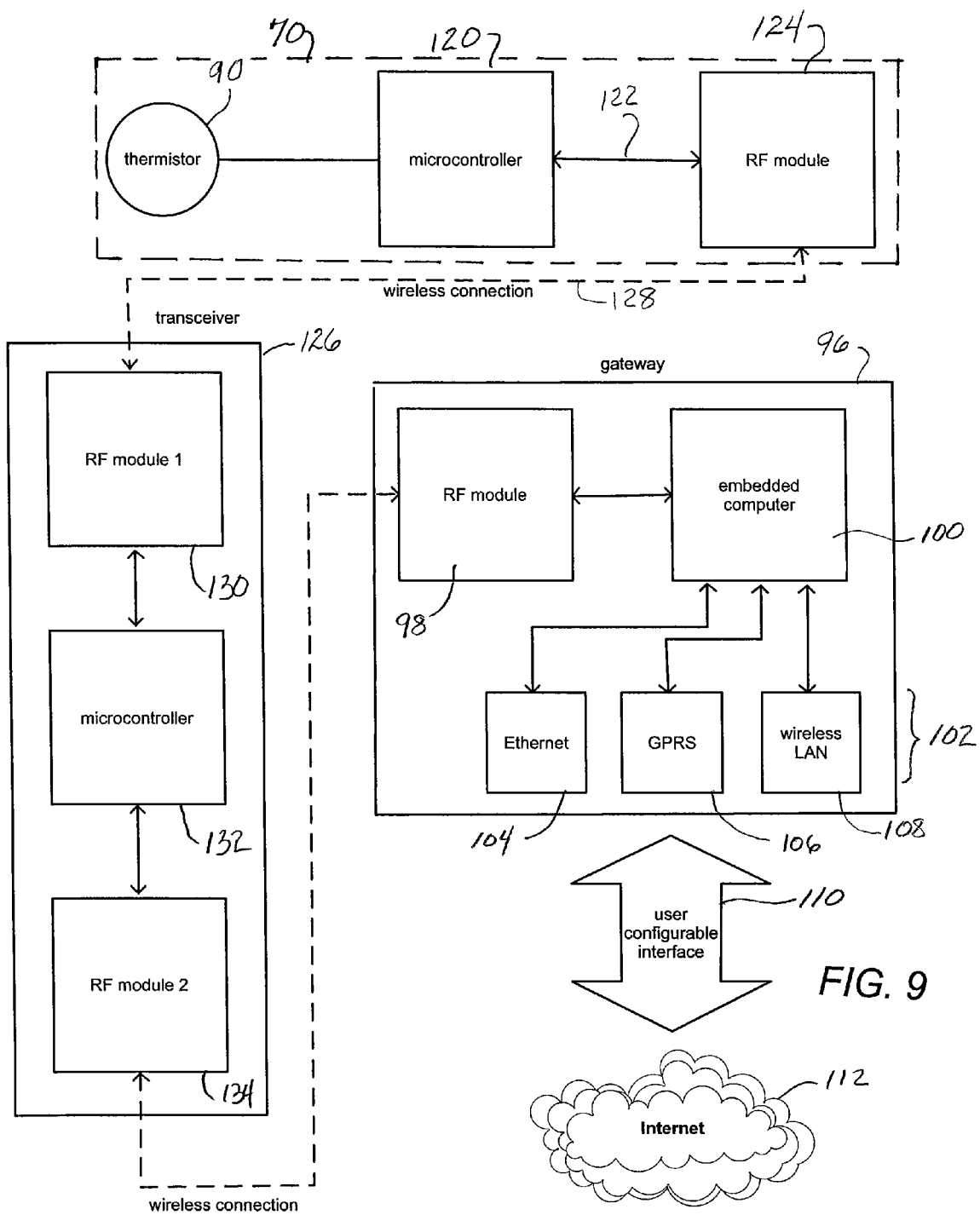
FIG. 9 is a block diagram of the flow of temperature data from the internal temperature sensor of the PPE shown in FIG. 1, comprising a mouth guard, through processing, wireless transmitting, receiving, and further transmitting electronics to permit remote monitoring of the internal temperature of the person wearing the mouth guard.

FIG. 9 provides a block diagram of data processing, transmission, and distribution of that data related to the vital signs monitor system 70 mounted in the PPE 72 shown in FIGS. 6 and 7. In particular, the thermal sensor 74 embedded in the mouth guard 72 (FIGS. 6 and 7) may take the form of a thermistor 90. The output of the thermistor is directed to a microcontroller 120 that among other things provides a serial temperature data output 122 comprising the information from the temperature signals obtained from the thermistor. The microcontroller polls the thermistor 90 for temperature data at predetermined intervals and controls the RF module 124 to remain in the power saving mode unless temperature data is present. In one embodiment, the microcontroller 120 is programmed to look for temperature signals from the thermistor 74 that indicate that the thermistor has now been placed into contact with a wearer and temperatures at or close to body temperature are now being sensed. Once this occurs, the microcontroller processes that thermistor signals into a serial data stream and controls the RF module 124 to turn "on" and to transmit that data. The RF module 124 comprises a Class 3 low power Bluetooth protocol transmitter in one embodiment in which the transmission range is approximately one meter. Because the vital signs monitor system 70 is meant to be small and unobtrusive, the power source comprises a single coin cell battery. This battery can have a life of between five to eight months when used in the power saving circuit described above.

The temperature data transmitted by the RF module 124 in the vital signs monitor system 70 is meant to be at a low power level so that the small and unobtrusive monitor system conserves its internal battery power. In the present embodiment, a transceiver 126 located on the wearer of the mouth guard 22, preferably also located in PPE, is used to receive the low power temperature data signals and retransmit that data at a much higher power level for reception by a remote receiver or receivers. The transceiver may have a larger power supply, such as AA batteries, enabling a longer range of transmission. Although not shown specifically in FIG. 5, the RF module 66 in the helmet 60 could take the form of the transceiver 126 shown in FIG. 9. However, in another embodiment, depending on the application and the technology used, the RF module 124 of the mouth guard may be used for direct transmission of the temperature data to the remote receiver or receivers.

The transceiver 126 mounted in the helmet 60 of the embodiment of FIG. 5, or in other PPE in other embodiments, includes a first RF module 130, a microcontroller 132, and a second RF module 134. In this embodiment, the first RF module 130 comprises a low power, short range Bluetooth Class 3 receiver. The range may be confined to one meter or less. The purpose of the first RF module 130 is to receive any data transmissions from the RF module 124 in the vital signs monitor system 70. The microcontroller 132 remains in a low power mode in which it continuously monitors the first RF module 130 for the receipt of any signals from the vital signs monitor system 70. Upon detecting that signals have been received, the microcontroller 132 switches to full power mode in which it receives the signals, processes them into the format for remote transmission, and forwards those signals to the second RF module 134 which it also controls to turn to the "on" state. The second RF module 134 then transmits the data signals over a much longer range, such as one-hundred meters, to the remote receiver or receivers.

As in FIG. 8, a gateway 96 is provided in FIG. 9. The gateway includes an RF module 98 that receives the RF transmission from the helmet 60, either in Bluetooth or Zigbee or other protocol, and provides the received signals containing temperature data to an embedded computer 100. That computer or other processing device then makes the temperature data available to one or more network or communication devices 102. In the case shown in FIG. 9, the embedded computer makes the temperature data signals available to an Ethernet 104, a general packet radio service 106 (GPRS), and/or a wireless local area network 108 (LAN). More or fewer or different communication devices 102 may be provided depending on the application. A user configurable interface 110 is then used to control access by and to the gateway 96. The gateway communicates the temperature data with a network, such as the Internet 112.

In the above embodiments, size, weight, and power conservation are given priorities. The vital signs systems are designed to be small and unobtrusive, as well as light. To conserve battery life, the circuits have power conservation features. Devices may remain in a "sleep" mode at which power consumption is low or almost zero. When a monitoring component senses the existence of particular data, it may "awaken" other devices in the circuit which will now perform their functions, but at a higher power level than when in the "sleep" mode. Those devices may automatically return to "sleep" mode under certain predetermined conditions, such as the failure to receive any data or commands for a predetermined length of time. In one embodiment such as that shown in FIG. 9, the vital signs monitor system 70 does not have an on/off switch. It remains continually "on", although in a very low power mode until operation is required by its sensing the existence of a predetermined condition, such as the data signals provided by a thermal sensor, as discussed above. By this design, the size, expense, and extra weight of an "on/off" switch are avoided. Furthermore, energy conservative transmission protocols are used, such as Zigbee and/or Bluetooth. Other data transmission protocols may be employed to accurately transmit the vital signs data yet keep power consumption low.

Figure 10:
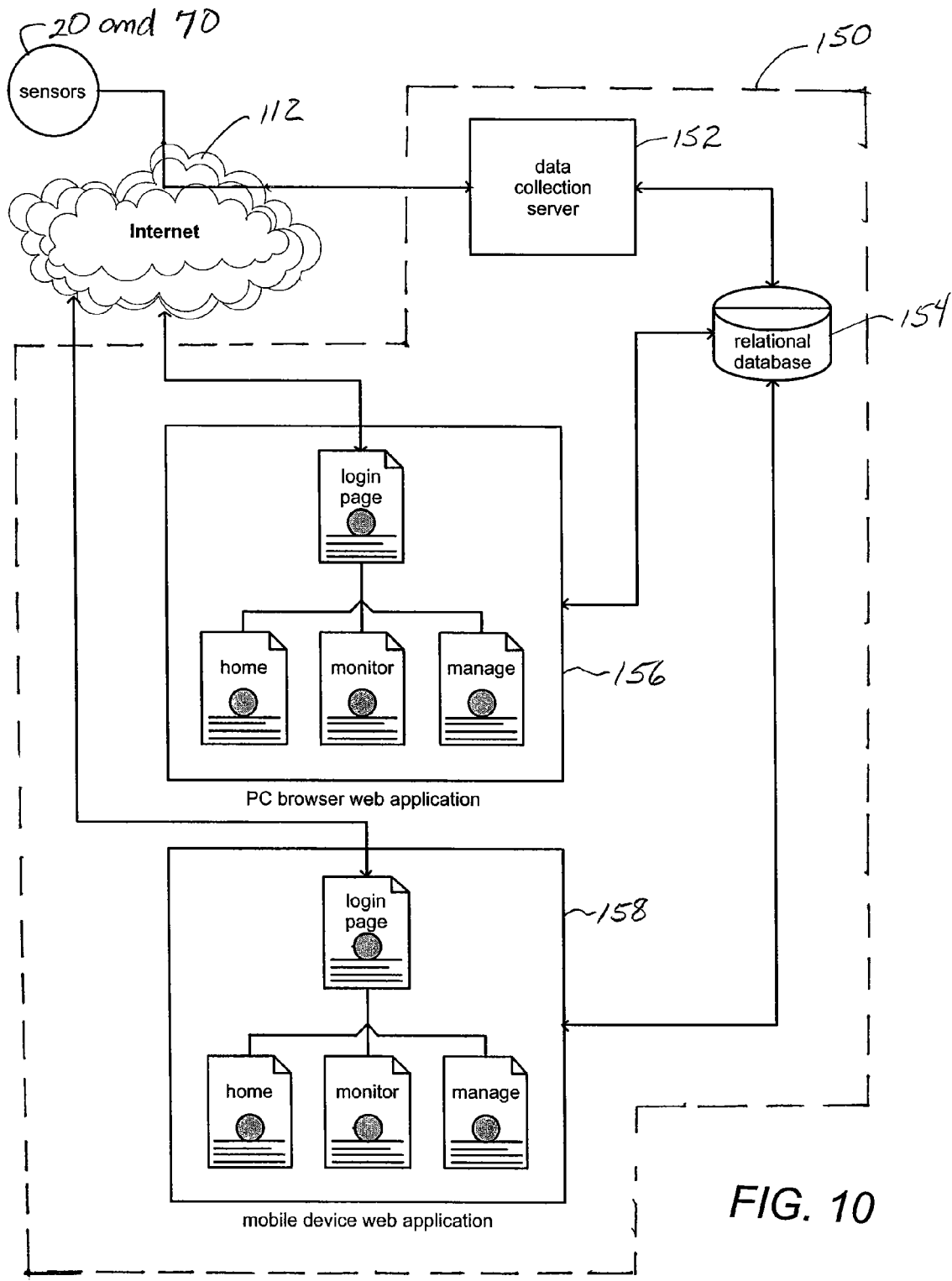
FIG. 10 is a diagram of the vital signs data collection by a server over a data network system, such as the Internet, the creation of a vital signs data base, access to that data base through multiple applications, and access to those applications remotely through a data network system.

Referring now to FIG. 10, a data collection, organization, and access system 150 is provided. In this embodiment, a data collection server 152 is connected with a network, such as the Internet 112, and receives temperature data. Such data provided by the vital signs monitoring systems 20 and 70 discussed above and shown in other drawings typically include identifications of the people being monitored and the vital signs data taken of them. The server 152 receives that data and organizes it into a relational data base stored in a storage device 154. That data base is accessible, in this embodiment, through two exemplary applications. The first is a personal computer browser web application 156 and the second is a mobile device web application 158. The first application 156 has full functionality in which the vital signs of numerous people can be monitored at once and multiple organizations of data and multiple reports may be generated. The second application 158 however has limited functionality. In the second application 158, which is designed for hand held devices such a smart telephones, the user may only be able to monitor the vital signs of a single person. This is due to the computing and memory constraints typical of mobile devices. These two applications are made available to the network, such as the Internet 112, and to numerous client devices.

Figure 11:
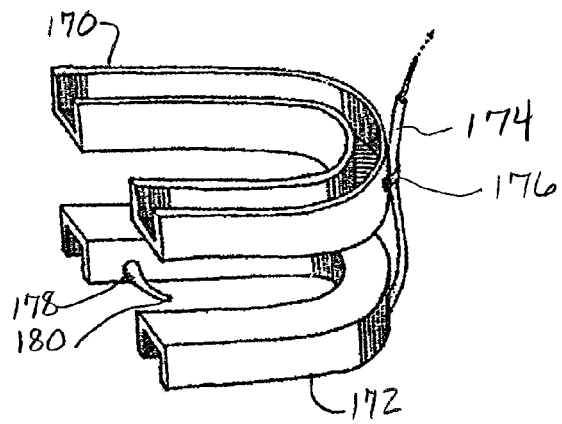
FIG. 11 is a perspective view a mouth guard comprising in this case, separate upper and lower mouth guard components, the lower mouth guard component having a thermal sensor extending inwardly so that it will be positioned under the tongue of a wearer when the mouth guard is placed in position, to continually sense the temperature of the wearer, and showing an example of a route for an electrical conduit used to conduct electrical signals representative of the sensed temperature extending from the front of the lower mouth guard and through a loop in the upper mouth guard so that the wearer can open his or her mouth to breathe while the temperature sensing continues.
Figure 12:
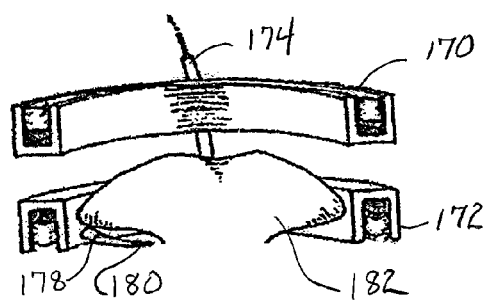
FIG. 12 is a rear view of the mouth guard of FIG. 11 showing the placement of the thermal sensor under the tongue of the wearer.
Figure 13:
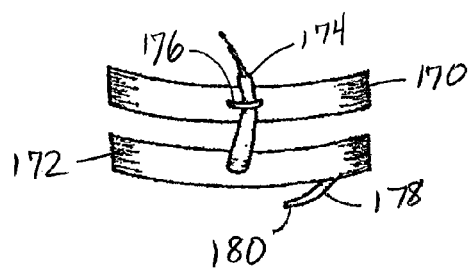
FIG. 13 is a front view of the mouth guard of FIG. 11 showing the angle of the thermal sensor in relation to the lower mouth guard component and showing the electrical wire route above a cutout in the mouth guard for the passage of breathing air for the wearer.

FIGS. 11 through 13 show an embodiment of an upper 170 and lower 172 mouth guard. A thermal conduit 174 runs through an upper mouth guard loop 176 to the lower mouth guard to allow for the wearer to open his/her mouth to breathe or for other purposes, and continue to transmit oral temperature. The thermal conduit 174 runs from the front of the mouth guard up to the helmet 60 faceguard shown in FIG. 5 and then on to the helmet RF module 66 to transmit temperature signals. The thermal conduit 174 runs through the lower mouth guard 172 to the left rear molars and then comes out of the mouth guard under the tongue with a semi-rigid non-toxic polymer feed 178 to keep the thermal sensor 180 continuously in the place under the tongue 182.

Figure 14:
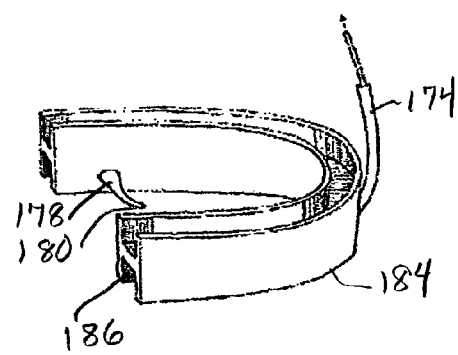
FIG. 14 is also a perspective view of personal protective equipment, in particular a mouth guard for protecting the wearer against concussion, the mouth guard comprising a single piece that receives both the upper and lower rows of teeth of a wearer, referred to as a "dual" mouth guard, showing the thermal sensor location, and the electrical wire or wires used for conducting the sensor signals that are representative of the temperature sensed.
Figure 15:
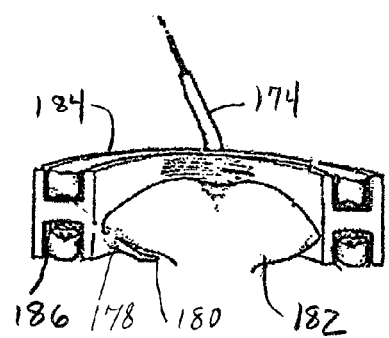
FIG. 15 is a rear view of the mouth guard of FIG. 14 showing the placement of the thermal sensor under the tongue of the wearer.
Figure 16:
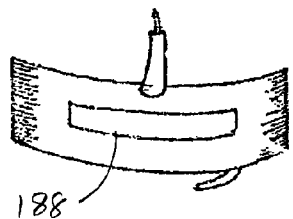
FIG. 16 is a front view of the mouth guard of FIG. 14 showing the angle of the thermal sensor in relation to the integrated mouth guard and showing the electrical wire location above a cutout in the mouth guard for the passage of breathing air for the wearer.

FIGS. 14-16 show a dual upper/lower mouth guard 184 in which the thermal conduit 174 runs through the lower mouth guard portion 186 to the left rear molars and then comes out of the mouth guard under the tongue 182 with a semi-rigid non-toxic polymer feed 178 to keep the thermal sensor 180 in place under the tongue. The thermal conduit runs from the front of the mouth guard up to the helmet 60 faceguard and then onto the RF module 66 (FIG. 5) in the helmet to transmit the sensed oral temperature. The front of the mouth guard has a cutout 188 for air to pass for breathing.

The thermal sensor 180 rests underneath the tongue 182 when wearing either of the mouth guards of FIGS. 11-13 or of FIGS. 14-16. Other designs for locating the sensor are possible.

Figure 17:
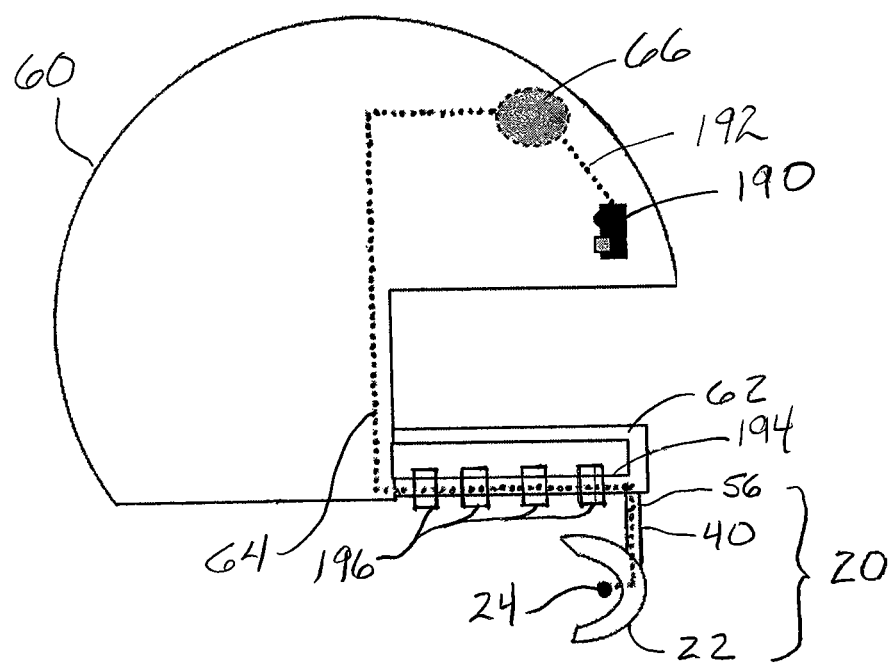
FIG. 17 is a side view of a helmet with an RF transceiver for transmitting vital signs data to a remote location, an RPO (reflective SPO$_2$ sensor) directed at the head of the helmet wearer to sense the wearer's oxygen saturation, a mouth guard as shown in FIGS. 1 through 4 having a thermal sensor for contact with internal tissues of the wearer to sense the wearer's temperature, and wiring to connect the mouthpiece with the helmet, in this case through the faceguard.

Turning now to FIG. 17, the helmet 60 of FIG. 5 is shown with the hard-wired and tethered vital signs temperature sensor system 20 of FIGS. 1 and 2. That vital signs sensor system 20 is tethered 56 to the face mask 62 as described in detail above. Also, the helmet RF module 66 is shown. However, in this embodiment, an additional, or second, vital signs monitor system 190 is included. A reflective SPO$_2$ (referred to herein as "RPO" or reflective pulse oximetry) sensor system 190 is mounted inside the helmet to rest on the forehead of the helmet wearer and sense the oxygen saturation of the wearer's blood. The RPO system of FIG. 17 is configured to provide not only oxygen saturation, but also pulse or heart rate. The RPO sensor system provides the oxygen saturation and heart rate data 192 to the RF module 66 for transmission to a remote location, as is described above in relation to the vital signs temperature data. An RPO system found to be usable is part no. IM1-100 from Hall Ryan Laboratories, Van Nuys, Calif.

The wiring 62 that conducts temperature data from the first vital signs sensor system 20 is tied to an inner area 194 of the helmet faceguard 62 with either permanent or releasable ties 196. Additional wiring to the RF module 66 from the face guard may be located between the outer helmet shell and the lining. Although not shown, a plug and socket connection with the helmet wiring 64 may be used so that the mouth guard vital signs monitoring system 20 is detachable from the helmet. It should be noted that the arrangement shown in FIG.

17 comprises only an exemplary embodiment. The vital signs monitoring system 70 of FIGS. 6 and 7 may be used in which there is a wireless communication between the mouth guard sensor system 70 and the RF module 66 of the helmet.

The RF Module 66 is therefore configured to receive temperature data from the first vital signs monitoring system 20, and oximetry and/or heart rate or pulse data from the second vital signs monitoring system 190. The RF Module 66 is configured to process this received data into the appropriate format for transmission to a remote location.

Other transmitting means may be used at the PPE for transmitting vital signs data to a remote receiver, such as infrared, optical, Bluetooth, microwave, or other. RF transmission is just one embodiment. In another embodiment, the helmet 60 may contain memory (not shown) for storing all sensor data. The stored data may later be downloaded through a suitable access means to the memory, for later analysis. Furthermore, the connection between the vital signs system 20 of FIGS. 1 through 4 and the RF module 66 located in the helmet is shown and referred to as "wired." While "wired" or "wiring" in general refers to insulated conductors used to carry electricity, it is meant herein to be broader and refer to "wired communication" in general. That is, means other that electrical devices for conducting data are included, such as, but not limited to, fiber-optic communication.

By means of the wireless transmission described above, heart rate, oxygen saturation, and body temperature data of the wearer of the PPE can be monitored by a person on the side lines of a field in which a sport is played to detect the possible onset of heat exhaustion or other malady. In one embodiment, the vital signs data is transmitted through the described gateway 96 to the described data collection, organization, and access system 150 (FIG. 10). Medical personnel on the side lines of the field sport can access this data through an Internet 112 connection to the data collection, organization, and access system. In another embodiment, field medical personnel may be able to directly receive the transmitted data from each PPE wearer and monitor the players' vital signs with a computer configured by a suitable program.

Athletes, as an example, will use the mouth guard while participating in contact sports, for measurement of their vital signs. An indicator at a remote location (e.g., the side line) will provide a visual and/or audible indication when the vital signs of a particular person indicate an out-of-normal condition. The data obtained from the sensors are transmitted to the side lines or downloaded from the helmet on the sidelines. As such, coaches and others can monitor the athletes to determine if an athlete is being affected by heat stress or other stress. Based on this information, the athlete can then be removed from the game if necessary before injury occurs. Another application is the transmission of data concerning fire fighters or other public safety personnel. The well-being of fire fighters during their activities in fighting fires may be monitored on the street below the burning building, for example, and action taken if needed. Many other applications exist for the system and method of the invention.

The mouth guard or mouth guards shown in FIGS. 11-16 are sized to fit in the mouth such that it or they cover the upper and lower teeth. Each mouth guard is preferably custom fit to the mouth of the athlete to ensure an accurate fit. The mouth guard is formed from a rigid plastic or other suitable material that is capable of withstanding forces generated by the athlete's teeth contacting the upper and lower surfaces of the mouth guard while participating in contact sports. The interior of the channel in one embodiment has a liner formed from a softer material (e.g., silastic, silicone or the material that is durable and protective). The liner of softer material prevents damage to tooth enamel. The mouth guards shown in the drawings include only a single temperature sensor but in another embodiment, a plurality of sensors may be used. In FIG. 17 and additional vital signs sensor is used. Other vital signs sensors may be used at the same time with a wearer of PPE. A mouth guard having a temperature sensor is available from Hall Ryan Laboratories, Van Nuys, Calif., having part no. TSM-100.

The tether 56 described above in relation to FIGS. 1 through 5 and others, includes the connector strap 50 to secure the mouth guard to a protective helmet or headgear, as shown for example in FIGS. 5 and 17. The distal end of the connector strap may include the connection configuration shown in FIGS. 3 and 4 or others, such as a snap fastener assembly. The free end of the connector strap may form a loop around a portion of the faceguard of the helmet to secure the mouth guard assembly to the helmet as was discussed. The snap fastener assembly may be releasable so that the mouthpiece assembly can be separated from the helmet. It is also contemplated that the fastener assembly may be a grommet or other more permanent fastener. It is also contemplated that the fastener assembly may directly attach the mouthpiece assembly to the side of the helmet.

The helmet may have various constructions according to the particular activity of the wearer. On the side lines, the player's helmet can be removed and if it contains memory that has stored sensor data, the helmet can then be connected to a computer to download information produced by the vital signs sensors in the helmet and elsewhere.

Although the mouth guards described above were custom made, both custom made and off-the-shelf styles may be used. Typically, the mouth guard is made or purchased and then the vital signs sensor or sensors are attached. However, other arrangements may be used that will fall within the scope of the present invention. Also, the arrangement shown in FIGS. 3 and 5 in which the controller module 40 is plugged into a socket on the helmet, is an exemplary configuration only. Other means of completing an electrical circuit may be used. Additionally, other means of providing a plug and socket arrangement can be devised. In a more detailed aspect, the tether, plug, and socket can be configured so that if enough load is applied, the tether will break away from the face guard 62 and the connector plug 48 will unplug from the helmet socket, resulting in minimal or no damage to the mouth guard vital signs monitoring system 20.

While the invention has been described in connection with what is presently considered to be the most practical and preferred embodiments, it is to be understood that the invention is not to be limited to the disclosed embodiments and elements, but, to the contrary, is intended to cover various modifications, combinations of features, equivalent arrangements, and equivalent elements included within the spirit and scope of the appended claims. The use of numerous sensors is possible. While a thermistor may be used as a temperature sensor, other technologies, currently existing or yet to be developed, may be used. It is contemplated that other sensors may be used provided the sensing device is compact. Furthermore, the dimensions of features of various components that may appear on the drawings are not meant to be limiting, and the size of the components therein can vary from the size that may be portrayed in the figures herein. Thus, it is intended that the present invention covers modifications and variations of the examples shown.

What is claimed is:

1. A vital signs monitoring system formed as an integral part of personal protective equipment for users, and configured to provide real-time vital signs data of a user, the vital signs monitoring system comprising:

a mouth guard configured to be worn over upper teeth in an oral cavity of a user to provide protection while leaving a roof of a user's mouth uncovered, the mouth guard having a front and a top;

a temperature sensor configured to provide temperature data representative of a sensed temperature, the temperature sensor mounted at the top of the front of the mouth guard in a position such that when the mouth guard is correctly worn by a user, the temperature sensor is automatically placed in contact with a mucosal membrane above a gum line and outside a breathing passageway, wherein the temperature sensor is protected from exposure to ambient air and moving breathing air;

a flexible tether having a first end attached to the front of the mouth guard, a second end configured for attachment to another equipment located outside a user's mouth, and a tether length between the first end and the second end, the tether length extending from the first end outside a user's mouth; and a controller module forming a part of the length of the tether at a position outside a user's mouth, the controller module comprising a power source, a processor, and a transmitter, the processor configured to receive the sensed temperature data from the temperature sensor and to control the transmitter to wirelessly transmit the received temperature data to a remote location.

2. The vital signs monitoring system of claim 1, further comprising a plurality of temperature sensors mounted to the top of the mouth guard such that when the mouth guard is correctly positioned on a user, each of the plurality of temperature sensors is positioned above a gum line and in contact with a mucosal membrane.

3. The vital signs monitoring system of claim 1, wherein the temperature sensor is embedded into the mouth guard at a position wherein when the mouth guard is correctly positioned on a user, the temperature sensor is automatically placed in contact with a user's mucosal membrane above a gum line.

4. The vital signs monitoring system of claim 3, wherein the temperature sensor is embedded into the mouth guard at a position wherein when the mouth guard is correctly positioned on a user, the temperature sensor is automatically placed in contact with a mucosal membrane at a front of an oral cavity above a gum line above a user's upper front teeth.

5. The vital signs monitoring system of claim 1, wherein the tether is releasably connected to the mouth guard such that the controller module can be reused while the mouth guard is replaced.

6. The vital signs monitoring system of claim 1, wherein the control module receives temperature data from the temperature sensor through a wired connection.

7. The vital signs monitoring system of claim 1, wherein the mouth guard has a channel that accepts a row of teeth, the row accepting teeth located on either side of an oral cavity, wherein the mouth guard has inner and outer sidewalls on inside and outside surfaces of a user's teeth respectively, the sidewalls being substantially parallel and substantially uniform in thickness wherein the mouth guard leaves a roof of a user's mouth uncovered.

8. The vital signs monitoring system of claim 7, wherein the temperature sensor is disposed on top of the outer sidewall of the mouth guard.

9. The vital signs monitoring system of claim 1, further comprising a second piece of personal protective equipment separate from the mouth guard having a second vital signs sensor, the second vital signs sensor comprising a reflective pulse oximetry sensor configured to sense a user's blood oxygen saturation and pulse rate at a location outside a user's mouth, the second vital signs sensor being mounted to the second piece of personal protective equipment and connected to a communication module located on the second piece of personal protective equipment such that a user's blood oxygen saturation and pulse rate are sensed by the reflective pulse oximetry sensor and data representing a sensed blood oxygen saturation and pulse rate are received from the reflective pulse oximetry sensor and transmitted to a remote location by the communication module.

10. The vital signs monitoring system of claim 9 wherein the second personal protective equipment comprises a helmet and wherein the second vital signs sensor is mounted to the inside of the helmet facing a user.

11. A temperature monitoring system formed as an integral part of personal protective equipment for users, and configured to provide real-time temperature data of a user, the temperature monitoring system comprising:

a mouth guard configured to be worn in an oral cavity of a user in a correct position to provide protection from concussions, the mouth guard having a channel that accepts a row of teeth, the channel having an interior liner formed from a soft material configured to prevent damage to tooth enamel, the channel having inside and outside walls that are substantially parallel with one another, the row having teeth on either side of an oral cavity, wherein when a user correctly wears the mouth guard a roof of a user's mouth is substantially uncovered;

a temperature sensor configured for providing temperature data representative of a sensed temperature, the temperature sensor mounted to the mouth guard in a configuration such that when the mouth guard is correctly worn by a user, the temperature sensor is automatically placed in contact with a mucosal membrane of an oral cavity, the mucosal membrane being located outside a breathing passageway and above a user's gum line, wherein the temperature sensor is protected from exposure to ambient air and moving breathing air;

a flexible tether having a first end attached to the front of the mouth guard, a second end configured for attachment to another equipment located outside a user's mouth, and a tether length between the first end and the second end, the tether length extending from the first end outside a user's mouth; and a controller module comprising a microcontroller, a power supply, and a communication module configured to receive the sensed temperature data through a wired connection with the temperature sensor and wirelessly transmit the received temperature data to a remote location, the controller module forming a part of the tether length at a location outside a user's mouth; and wherein the tether is mounted to the front of the mouth guard such that it is releasable from the mouth guard such that the controller module is reusable with another mouth guard.

12. The temperature monitoring system of claim 11, wherein the mouth guard comprises a thermal laminate.

13. The temperature monitoring system of claim 11, further comprising a second piece of personal protective equipment separate from the mouth guard having a second vital signs sensor, the second vital signs sensor being located outside a user's mouth and comprising a reflective pulse oximetry sensor positioned to rest on a forehead of a user.

14. The vital signs monitoring system of claim 13 wherein the second personal protective equipment comprises a helmet and wherein the second vital signs sensor is mounted to the inside of the helmet facing a user.

15. A method for monitoring a vital sign of a user who wears personal protective equipment, the method comprising:

mounting a temperature sensor to a mouth guard, the mouth guard configured to be worn in an oral cavity of a user in a correct position to provide protection to a user, wherein the sensor is mounted to the mouth guard in a position such that when the mouth guard is correctly worn by a user, the temperature sensor is automatically placed in contact with a mucosal membrane of an oral cavity, the mucosal membrane being located outside a breathing passageway, wherein the temperature sensor is protected from exposure to ambient air and moving breathing air;

sensing temperature at a position along a mucosal membrane above a gum line of a user's oral cavity;

communicating data representative of the sensed temperature through a wired connection;

connecting a first end of a flexible tether to the mouth guard and a second end of the tether to another equipment outside a user's mouth, the tether having a tether length between the first end and the second end, the tether length extending from the first end outside a user's mouth;

connecting a controller module to the wired connection so that the controller module receives the sensed temperature data, the controller module comprising a power source, a processor, and a transmitter;

processing the sensed temperature data from the temperature sensor;

forming a part of the tether's length at a position outside a user's mouth with the controller module so that the communication module is located outside an oral cavity; and controlling the transmitter to wirelessly communicate the sensed temperature data to a remote location.

16. The method for monitoring a vital sign of a user of claim 15 wherein the step of connecting the tether further comprises connecting the tether in a releasable manner so that the controller module is reusable with other personal protective equipment.

* * * * *